(12) United States Patent
Weinberg et al.

(10) Patent No.: US 6,432,405 B1
(45) Date of Patent: Aug. 13, 2002

(54) METHOD OF INHIBITING HIV INFECTION WITH CD44 AND ANTI-CD44 ANTIBODIES

(75) Inventors: J. Brice Weinberg; Barton F. Haynes, both of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/753,851

(22) Filed: Dec. 2, 1996

Related U.S. Application Data

(63) Continuation of application No. 08/047,068, filed on Apr. 16, 1993, now abandoned, which is a continuation of application No. 07/945,581, filed on Sep. 16, 1992, now abandoned, which is a continuation of application No. 07/682,518, filed on Apr. 9, 1991, now abandoned, which is a continuation-in-part of application No. 07/669,730, filed on Mar. 15, 1991, now abandoned.

(51) Int. Cl.$^7$ .................... A61K 39/395; C07K 14/705; C07K 4/00
(52) U.S. Cl. .................. 424/154.1; 424/130.1; 424/140.1; 424/141.1; 424/143.1; 424/144.1; 424/153.1; 424/173.1; 514/2; 514/8; 514/885; 514/12; 514/13; 514/14; 514/15
(58) Field of Search .................... 424/130.1, 140.1, 424/144.1, 154.1; 514/2, 8, 54, 12, 13, 14, 15; 530/300, 387.1, 388.11, 388.2, 388.22, 388.7, 388.73, 324, 326, 327; 536/55.1

(56) References Cited

U.S. PATENT DOCUMENTS 4,840,941 A * 6/1989 Ueno et al.
5,002,873 A * 3/1991 St. John et al. ............. 435/69.1
5,108,904 A * 4/1992 Landay ....................... 435/7.24
6,069,135 A * 5/2000 Falk et al.

OTHER PUBLICATIONS

1. Daar et al. PNAS 87: 6574–6578 (1990).*
2. Haynes et al. Science 271: 324–328 (1996).*
3. Fox Biotechnology 12: 128 (1994).*
4. Sommerfelt et al. J Gen Virol. 76: 1345–1352 (1995).*
ATCC Cell Lines and Hybridonas 8th Edition 1994 (ED) Hay ATCC Rockville, MD p. 416 only.*
1. Paul ed. Fundamental Immunol. Raven Press NY 1993 p 242.*
2. Rivadene Ira et al. AIDS Research and Human Retroviruses 11: 541–546 (1995).*
3. Sigma Chemical Co. Catalog 1992 p. 1119.*
1. Harris et al. Tibtech 11: 42–45 (1993).*
2. Shaffer Biotechnology Newswatch Oct. 4, 1993 p. 9.*
3. Edgington Biotechnology 10: 383–389 (1992).*
4. Fahey et al. Clin Exp Immunol 88: 1–5 (1992).*
5. Hirsch et al. NEJM 328: 1686–1695 (1993).*
6. Nicholson J. Immunol. 137: 323–329 (1986).*
7. Imt Sushita et al. AIDS Research & Human Retroviruses 6:193–203 (1990).*
8. Willerford et al. J. Immunol. 144: 3779–3783 (1990).*
9. Cuo et al. J. Immunol. 151: 2225–2235 (1993).*
Haynes et al., Springer Semin Immunopathol. vol. 11, pp. 163–185 (1989).*
1. Pearce–Pratt et al. Biol. Reprod. 54: 173–182 (1996).*
2. Dukes et al. J. Virol. 69: 4000–4005 (1995).*
3. Sigma Chemical Co. Catalog 1995 p. 1171 only.*
4. ATCC Cell Lines and Hybridomas 8$^{th}$ Ed 1994 American Type Culture Collection, Rockville MD p. 416 only.*

* cited by examiner

*Primary Examiner*—Phillip Gambel
(74) *Attorney, Agent, or Firm*—Nixon & Vanderhye P.C.

(57) ABSTRACT

The present invention relates to a method of inhibiting HIV infection of cells susceptible to HIV infection. The method comprises contacting such cells with an agent (such as an anti-CD44 antibody) that inhibits CD44-facilitated HIV infection of the cells.

12 Claims, 7 Drawing Sheets

METHOD OF INHIBITING HIV INFECTION WITH CD44 AND ANTI-CD44 ANTIBODIES

This is a continuation of application Ser. No. 08/047,068, filed Apr. 16, 1993, now abandoned; which is a Continuation of 07/945,581, filed Sep. 16, 1992, abandoned; which is a Continuation of 07/682,518, filed Apr. 9, 1991, abandoned; which is a CIP of 07/669,730, filed Mar. 15, 1991, abandoned.

This invention was made with Government support under Grant No. CA-28936 awarded by the National Institutes of Health. The Government has certain rights in this invention.

BACKGROUND OF THE INVENTION

1. Field of the Invention

The present invention relates to methods of suppressing T cell activation, inhibiting CD44-mediated cell adhesion and CD44-monocyte IL1 release, treating inflammation, and transporting a drug or cytotoxic agent to a site of inflammation.

2. Background Information

Recent work has defined the importance of cell adhesion molecules in immune cell function (reviewed in Springer (1990) Nature 346:425–434; Haynes et al. (1989) Springer Sem. Immunopathol. 11:163–185; Hemler (1988) Immunol. Today 9:109–113). Cell adhesion molecules have been described that are receptors for soluble molecules (Haynes et al (1984) Nature 312:763–766), receptors for viruses (reviewed in Springer (1990) Nature 346:425–434; Dalgleish et al. (1984) Nature 312:763–766; Klatzmann et al. (1984) Science 225:59–63), and ligands for other cell surface molecules (reviewed in Springer (1990) Nature 346:425–434; Haynes et al. (1989) Springer Sem. Immunopathol. 11:163–185; Hemler (1988) Immunol. Today 9:109–113).

On immune cells, cell adhesion molecules mediate a wide variety of normal cell functions including cell movement, adherence to other cells, adherence to extracellular matrix proteins, mononuclear cell homing and monocyte cytokine release (reviewed in Springer (1990) Nature 346:425–434; Haynes et al. (1989) Springer Sem. Immunopathol. 11:163–185; Hemler (1988) Immunol. Today 9:109–113; Haynes et al. (1989) Immuno. Today 10:423–428). The CD44 molecule has been of recent interest because this protein has multiple proinflammatory functions, exists in soluble form in serum and plasma, and regulates the function of other adhesion molecules (reviewed in Haynes et al. (1989) Springer Sem. Immunopathol. 11:163–185; Haynes et al. (1989) Immuno. Today 10:423–428).

The CD44 molecule is an 85 kd glycosylated molecule with N-terminal sequence homology to cartilage link proteins (Stamenkovic et al (1989) Cell 56:1057–1062; Goldstein et al (1989) Cell 56:1063:1072). Forms of CD44 of varying sizes have been described on many cell types (Haynes et al (1989) Immunol. Today 10:423–428, Stamenkovic et al (1989) Cell 56:1057–1062; Goldstein et al (1989) Cell 56:1063–1072; Jalkanan et al (1988) J. Immunol. 141:1615–1623). Variations in the size of CD44 isoforms have been suggested to be due to glycosylation differences, the addition of chondroitin sulfate molecules to CD44 (Jalkanan et al (1988) J. Immunol. 141:1615–1623), and in some cases, to alternative splicing of CD44 mRNA (Dougherty et al (1988) Exp. Hemat. 18:703, St. John et al (1989) Req. Immunol. 2:300–310). Three forms of CD44 have been identified on peripheral blood mononuclear cells (PBMC) (Hale et al (1989 Arth. Rhem. 32:22–30) and an 85 kd form (presumably a secreted form) has been identified in serum, plasma (Telen et al (1983) J. Clin. Invest. 71:1878–1886; Lucas et al (1989) Blood 73:596–600) and now synovial fluid.

Functionally, the CD44 molecule has been shown to be a central molecule involved in T lymphocyte adhesion, T lymphocyte activation and monocyte cytokine release (Haynes et al (1989) Immunol. Today 10:423–428; Jalkanen et al (1986) Science 233:556–558; Jalkanen et al (1987) J. Cell Biol. 105:983–990; Aruffo et al (1990) Cell 61:1303–1313; Miyake et al (1990) J. Exp. Med. 172:69–75; Lesley et al (1990) Exp. Cell Res. 187:224–233; Stamenkovic et al (1989) Cell 56:1057–1062; Goldstein et al (1989) Cell 56:1063–1072; Jalkanan et al (1988) J. Immunol. 141:1615–1623). The association of the CD44 intracellular domain with the cytoskeletal protein, ankyrin, and with the enzyme protein kinase C (PKC) (Kalomiris et al (1989) J. Biol. Chem. 264:8113–8119) has suggested a role for CD44 in signal transduction of surface events to intracellular molecules. Ligand binding to the CD44 molecule promotes T cell adherence to monocytes via other adhesion molecule pathways (ICAM-1/LFA-1 and LFA-3/CD2) (Denning et al; Koopman et al (1990) J. Immunol. 145:3589–3593) suggesting that CD44 can serve as a regulator of function of other adhesion molecules (reviewed in Haynes et al (1989) Springer Sem. Immunopathol. 11:163–185; Haynes et al. (1989) Immunol. Today 10:423–8).

Recent studies have demonstrated that the CD44 protein is the primary receptor for hyaluronate in rodents and humans (Aruffo et al (1990) Cell 61:1303–1313; Miyake et al (1990) J. Exp. Med. 172:69–75; Lesley et al (1990) Exp. Cell Res. 187:224–233). Both hyaluronate (Hiro et al (1986) Biochem. Biophys. Res. Comm. 140:715–722) and CD44 mAB (Denning et al (1989) J. Immunol. 142:2988–97; Webb et al Science, 249:1295) binding to monocytes induces monocyte IL1 release. On T cells, hyaluronate and CD44 mAB ligation of CD44 have disparate effects; CD44 mABs augment T cell triggering (Denning et al (1989) J. Immunol. 142:2988–97 ; Huet et al (1989) J. Immunol. 143:798–801; Shimuzu et al (1989) J. Immunol. 143:2457–2463) while hyaluronate suppresses T cell triggering (Anastassiades et al (1984) Rheumatol. 11:734–729). Finally, CD44 mabs and polyclonal anti-CD44 serum have been shown to inhibit the binding of lymphocytes to high endothelial venules in inflammatory sites such as synovium (Jalkanen et al (1986) Science 233:556–558; Jalkanen et al (1987) J. Cell Biol. 105:983–990; Jalkanan et al (1988) J. Immunol. 141:1615–1623), suggesting lymphocyte CD44 is one of several molecules involved in organ-specific lymphocyte homing. Thus, the hyaluronate receptor (CD44) molecule, by existing in several isoforms, and by virtue of wide cellular distribution, functional association with other adhesion molecules, and physical association with ankryin and PKC, is a multifunctional proinflammatory molecule involved in immune cell activation (reviewed in Haynes et al (1989) Immunol. Today 10:423–428).

Hyaluronate, the ligand for CD44, is an important component of synovial fluid and plays a critical role in maintaining high viscosity of synovial fluid in normal diarthroidal joints (reviewed in Schuber and Hammerman (1964) Bull. Rheum. Dis. 14:345–348; Castor et al (1966) Arth. Rheum. 9:783–794). In rheumatoid arthritis (RA) synovial fluid, hyaluronate concentration and degree of polymerization is decreased (Castor et al (1966) Arth. Rheum. 9:783–794). Reduction in synovial fluid hyaluronate concentration and degree of polymerization has been suggested to be an important factor leading to joint dysfunction and destruction in RA (Schubert et al (1964) Bull. Rheum. Dis. 14:345–348; Castor et al (1966) Arth. Rheum. 9:783–794), and potentially may decrease the immunosuppressive effect of hyaluronate on T cells (Anastassiades et al (1984) Rheumatol. 11:734–729).

Applicants have demonstrated that CD44 is upregulated in RA on many synovial cell types and that the level of CD44 present in synovial tissue is directly proportional to the degree of synovial inflammation in RA. Applicants have also demonstrated that CD44 is immunosuppressive to T cells. The present invention relates, at least in part, to a method of interdiction of proinflammatory functions of the CD44 molecule.

SUMMARY OF THE INVENTION

It is a general object of this invention to provide a method of treating inflammation.

It is a specific object of this invention to provide a method of suppressing T cell activation.

It is another object of the invention to provide a method of inhibiting CD44-mediated cell adhesion or CD44-mediated monocyte IL1 release.

It is yet another object of the invention to provide a method of transporting a drug or cytotoxic agent to a site of inflammation, and to compositions suitable for use in such a method.

Further objects and advantages of the present invention will be clear from the description that follows.

In one embodiment, the present invention relates to a method of suppressing T cell activation in an human comprising administering to the human CD44 protein peptide or derivative thereof in an amount sufficient to suppress T cell activation.

In another embodiment, the present invention relates to a method of inhibiting CD44-mediated cell adhesion or CD44-mediated monocyte IL1 release in an animal comprising administering to the human CD44 protein or peptide or derivative thereof in an amount sufficient to inhibit CD44-mediated cell adhesion or CD44-monocyte IL1 release.

In a further embodiment, the present invention relates to a method of treating inflammation in an human comprising administering to the human CD44 protein or peptide or derivative thereof in an amount sufficient to reduce the inflammation.

In another embodiment, the present invention relates to a method of transporting a drug or cytotoxic agent to a site of inflammation in an human comprising administering to the human CD44 protein or peptide or derivative thereof linked to the drug or cytotoxic agent. In a preferred embodiment, the CD44 protein or peptide or derivative thereof and the drug or cytotoxic agent are incorporated into a liposome.

BRIEF DESCRIPTION OF THE DRAWINGS

FIG. 2A shows Western blot of OA synovium no. 198 (inflammation score=3), trauma synovium no.229 (inflammation score=5), and RA synovium nos. 7, 154, and 86 (inflammation scores 13, 21, and 18, respectively). FIG. 2B shows the area under the densitometry curve (arbitrary units) of the CD44 bands shown in FIG. 2A.

FIG. 5A compares CD44 levels in gout versus trauma synovial fluid. Control lanes A and B as in FIG. 3. Lane B shows CD44 in fluid 11 (CD44 level=1.0) and lane D shows CD44 in fluid 32 (CD44 level=3.79). Band at 40 kd in lanes A, B, and C is a non-specific band not present in lane D for technical reasons. FIG. 5B compares CD44 levels in psoriatic arthritis versus trauma synovial fluid. Control lanes A and C as in FIG. 3. Lane B is trauma fluid no. 11 (CD44 level=1.0) lane D is psoriatic arthritis synovial fluid no.100 (CD44 level=7.0).

DETAILED DESCRIPTION OF THE INVENTION

Figure 1A:
FIGS. 1A, B, and C are from trauma synovium no. 229 (inflammation score=5). Panel A shows hematoxylin and eosin (H and E) stain, panel B shows reactivity of synovium with anti-fibronectin mAb FN15 (fibronectin index=2+) and panel C shows reactivity of synovium with anti-CD44 mAb AlG3 (CD44 index=1+).
Figure 1B:
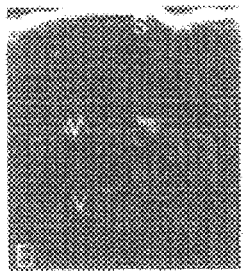
FIG. 1. Upregulation of CD44 Expression in RA But Not in Non-inflammatory OA or Trauma.
FIGS. 1D, E, and F are from OA synovium no. 36 (inflammation score=5). Panel D shows H and E stain, panel E shows fibronectin expression (fibronectin index=1+), and panel F shows CD44 expression (CD44 index=1+). FIGS. G, H, and I are from RA no. 86 (inflammation score=18). Panel G shows H and E stain, panel H shows fibronectin expression (fibronectin index=4+) and panel I shows CD44 expression (CD44 index=3+). FIGS. J, K, and L show RA synovium no. 7 (inflammation score=13) with pannus formation. FIG. J shows H and E stain, FIG. K shows fibronectin expression (fibronectin index=4+) and FIG. L shows CD44 expression (CD44 index=4+). All panels showing fibronectin and CD44 expression are indirect IF. All panels 400X.
Figure 1C:
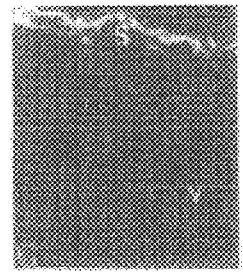
Figure 1D:
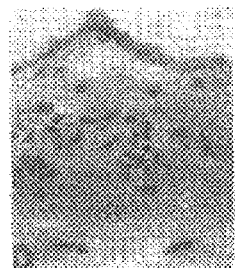
Figure 1E:
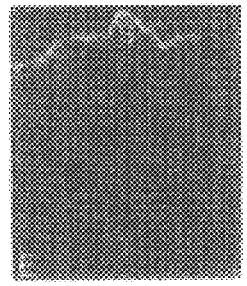
Figure 1F:
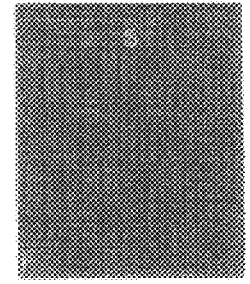

The present invention relates to a method of treating inflammation and immune-mediated tissue damage, such as occurs, for example, in the course of autoimmune diseases.

In one embodiment, the present invention relates to a method of suppressing T cell activation in an human comprising administering to the human the CD44 protein, or derivative or peptide portion thereof, in an amount sufficient to effect suppression. Examples of CD44 peptides suitable for use in the present method include those sets forth in Table 1.

TABLE 1

Examples of CD44 Peptides That Can Be Used To
Inhibit CD44-Mediated Immune Cell Functions

| Peptide no. | Sequence | aa | |
|---|---|---|---|
| CD44-1 | (C)EKNGRYSISRTEAADCCKAFN | (SEQ ID NO:1) | 37–57 |
| CD44-2 | (C)NTSQYDTYCFNASAPPEEDCTS | (SEQ ID NO:2) | 110–131 |
| CD44-3 | (C)RDGTRYVQKGEYRTNPEDIYPSNPTDDDVSS | (SEQ ID NO:3) | 150–180 |
| CD44-4 | (C)RDGTRYVQKGEYRINPEDIYPSNPTDDDVSSGSSSERSSTS | (SEQ ID NO:4) | 150–190 |
| CD44-5 | (C)YRTNPEDIYPSNPTDDDVSS | (SEQ ID NO:5) | 161–180 |
| CD44-6 | (C)TVHPIPDEDSPWITDSTPRI | (SEQ ID NO:6) | 200–219 |
| CD44-6a | DSPWITDSTDRIFATRDQDTI | (SEQ ID NO:7) | 208–227 |
| CD44-7 | (C)ATRDQDTFHPSGGSHTTHESESDGHSHGSQEGGAN | (SEQ ID NO:8) | 221–255 |
| CD44-8 | (C)RDGIRYVQKGEY-PSNPTDD-TSGGYIFYTF | (SEQ ID NO:9) | 150–161 |
| | | (SEQ ID NO:10) | 170–177 |
| | | (SEQ ID NO:11) | 189–198 |
| CD44-9 | LCLVPLSLAQIOLNITCRFAGVFHVEKNGRY | (SEQ ID NO:12) | 12–42 |
| CD44-10 | LCKAFNSTLPTMAQMEKALSIGFETCRY | (SEQ ID NO:13) | 52–79 |
| CD44-11 | CRYGFIEGHVVIPRIHPNSIC | (SEQ ID NO:14) | 77–97 |
| CD44-12 | RYGFIEGHVVIPRIHPNSI | (SEQ ID NO:15) | 76–96 |
| CD44-13 | LTYNTSQYDTY | (SEQ ID NO:16) | 107–117 |

Sequences from Stamenkovic et al, Cell 56:1057–1062, 1989.

Administration can be by injection or topical application (for example topically applied to the eye). Injection can be made directly into a skin lesion.

An additional form of the CD44 molecule that may be used as an immunosuppressive agent is a recombinantly produced CD44 molecule or a portion of the CD44 molecule produced by recombinant DNA technology. An example of such a form of CD44 has been reported by Aruffo, A et al Cell 61:1303–1313, 1990. This form of CD44 has been recombinately engineered to contain portions of the immunoglobulin protein constant domains. The addition of immunoglobulin domains to the extracellular domain of CD44 yielded in molecule called CD44-Rg-2 that has the properties of being secluded by COS cells when a plasmid containing this CD44-Rg2 gene was transfected into COS cells (Aruffo et al. Cell 61:1303–1313, 1990). The presence of immunoglobulin on the extracellular domain of CD44 would also have the potential advantage of increasing the circulating half-life of the CD44 molecule when administered to humans or animals.

Production of CD44-Rg-2 fusion construct: CD44-Rg-2 plasmid can be transfected into COS cells using DEAE dextran as described in Seed and PNAS 84: 3365–3369, 1987 and Aruffo, A et al Cell 61: 1303–1313, 1990. Semi-confluent COS cells plated on 100 mm plates will be transfected. Twelve hours after transfection, cells are trypsinized, seeded onto fresh 100 mm dishes and allowed to grow for 7–10 days. On the fourth day 5 ml fresh media, 10% calf serum are added per dish. Supernatants are harvested and stored at 4° C.

Purification of CD44-Rg protein: Twelve hours following transfection, a fraction of the COS cells transfected are seeded into flasks. Thirty-six hours post-transfection, the cells are washed with PBS and overlayed with cysteine-methionine media for 30 min. [$^{35}$Methionine and [$^{35}$S] Methionine and [35S] Cysteine will be added to a final concentration of 150 µCl/ml, and the cells will be allowed to incorporate the label overnight. The supernatants will be harvested and incubated with 200 µl of protein A-Trisacryl at 4° C. for 12 hours. The beads will be collected by centrifugation and washed in 10 ml of PBS, 1 Nonidet P-40. The beads will then be eluted 200 µl of 1% SDS.

In another embodiment, the present invention relates to a method of inhibiting various types of cellular interactions including macrophage T cell interactions and lymphocyte and macrophage interactions with endothelial cells. The invention further relates to a method of inhibiting CD44-monocyte IL1 release. These methods also involve the administration of an effective amount of the CD44 protein or derivative or portion thereof to an animal in need of such treatment.

CD44 protein suitable for use in the present method can be isolated from synovial tissue (preferably, human synovial tissue) or the protein can be produced recombinantly. Synthetic peptides reflective of discrete regions of the CD44 molecule can be made by standard techniques.

One skilled in the art will appreciate that the amounts to be administered for any particular treatment protocol can readily be determined. The CD44 protein, peptide or derivative can be administered together with a pharmaceutically acceptable carrier.

In yet another embodiment, the present invention relates to a method of transporting a drug or cytotoxic agent to a site of inflammation in an animal comprising administering to the animal the CD44 protein, or peptide or derivative thereof, linked, preferably covalently, to the drug or cytotoxic agent.

Examples of drugs to be targeted to organ- specific sites of inflammation are non-steroidal anti-inflammatory agents, forms of glucocorticosteroids, and cytoxic agents such as cyclophosphamide. By either incorporating these agents in liposomes bearing CD44 molecules, or by physically linking CD44 molecules to these drugs, one could achieve selective targeting or homing of the drug-CD44 complexes to sites of upregulated CD44 expression, that is sites of inflammation.

In a further embodiment, the present invention relates to a method of transporting a drug or cytotoxic agent to a site of inflammation in an animal comprising administering to the animal CD44 protein, or peptide or derivative thereof, and a drug or cytotoxic agent wherein both are incorporated into a liposome.

The present invention is described in further detail by the following non-limiting Examples.

EXAMPLES

The following protocols and experimental details are referenced in the Examples that follow:

Synovial Tissue and Synovial Fluid

Synovial tissue was obtained as discarded tissue from the Duke University Department of Pathology at the time of joint surgery. Synovial fluid was obtained as discarded fluid from the Duke University Clinical Immunology Laboratory at the time of arthrocentesis.

Histopathologic Techniques

Synovial tissues were processed, cut, and studied in indirect immunofluorescence (IF) assays as previously described (Hale et al (1989) Arth Rhem. 32:22–30). An inflammation score was generated for each synovium using light and IF microscopy based on the degree of T, B, and monocyte infiltration, vessel proliferation, fibroblast and synovial lining cell proliferation as described (Rooney et al (1988) Arth. Rhem. 31:956–963, McCachren et al (1990) J. Clin. Immunol. 10:19–27). The degree of reactivity of CD44 and anti-fibronectin antibodies was graded 1+ to 4+ with 1+ signifying reactivity with $\leq 25\%$ of synovial tissue reactive, 2+>25% and $\leq 50\%$ of synovial tissue area reactive, 3+>50% and $\leq 75\%$ of synovial tissue area reactive, and 4+>75% of synovial tissue area reactive.

Monoclonal Antibodies

The following monoclonal antibodies were used: CD44 (AlG3 and A3D8) (Haynes et al. (1983) J. Immunol. 131:1195–1200, Telen et al. (1983) J. Clin. Invest. 71; 1878–1886), anti-fibronectin (FN-15, Sigma, St. Louis, Mo.) 187.1 rat anti-mouse kappa chain (ATCC, Rockville, Md.), 35.1 (CD2) (Martin et al. (1983) J. Immunol. 131:180–185), 9-1 (CD2) (Bernard et al. (1986) Hum. Immunol. 17; 388–405), and P3x 63/Ag8 ascites fluid as a negative control.

Flow Cytometry

Flow cytometric analysis was performed on synovial fluid cells using a Becton-Dickinson (Mountain View, Calif.) FACS STAR PLUS flow cytometer in IF assays, as described (Hale et al. (1989) Arth Rhem. 32:22–30, Haynes et al (1981) New Engl. J. Med. 304:1319–1323).

Characterization of CD44 from Synovial Tissue

Synovial tissue was thawed, homogenized with a Dounce homogenizer in 0.6–1.0 ml extraction buffer (10 mM Tris pH 8.0, 150 mM NaCl, 1% Triton X-100, 20 µg/ml soybean trypsin inhibitor, 1 mM iodoacetamide, and 1 mM PMSF), and centrifuged, (15000 rpm×1 minute). The protein content of supernatants (tissue extracts) was determined using a copper/bicinchoninic acid assay (McCachren et al. (1990) J. Clin. Immunol. 10:19–27) (BCA Protein Assay, Pierce, Rockford, Ill.). Tissue extracts were analyzed by SDS-PAGE on 7% or 10% mini-gels (Mini-Protean II, Biorad Laboratories, Richmond, Calif.), followed by Western blot analysis using alkaline phosphatase-conjugated goat anti-mouse immunoglobulin along with the color development substrates BCIP (5-bromo-4-chloro-3 indolyl phosphate) and NBT (nitro blue tetrazolium) as developing reagents.

Western Blot Analysis of Tissue Extracts

To compare band densities from a given experiment, blots were photographed using TechPan film and resulting positive film densities measured using a laser densitometer. CD44 in trauma synovial tissue was given the value of 1 and the level of CD44 in RA and OA fluids were expressed as a ratio using the equation, CD44 ratio=CD44 in RA or OA Tissue/CD44 in Trauma Tissue.

Analysis of Synovial Fluid for CD44 Protein

Synovial fluid specimens were centrifuged, aliquoted, and stored at −80° C. until processed. CD44 protein was immunoprecipitated from aliquots of synovial fluid which were precleared by incubation with P3-SEPHAROSE (control) beads, then precipitated with either A3D8-SEPHAROSE or P3-SEPHAROSE. Immunoprecipitates were removed from the beads by boiling in 0.06 M Tris pH 6.8, 10% glycerol, 2% SDS and analyzed by SDS-PAGE and Western blot analysis using alkaline phosphatase conjugated 187.1 rat anti-mouse immunoglobulin. The amount of CD44 in trauma synovial fluid was given the value of 1 and the level of CD44 in RA and OA fluids were expressed as a ratio using the equation, CD44 ratio CD44 in RA or OA Fluid/CD44 in Trauma Fluid Band densities of CD44 in gels were determined as for tissue above.

Purification of Soluble CD44 Protein

CD44 (A3D8) and control YgGl (P3X63/Ag8) antibodies were conjugated to CNBr-activated SEPHAROSE CL 4B (Pharmacia, Piscataway, N.J.) (3.0 mg IgG/ml gel). HuT 78 T Cell (CD44+) lysate was solubilized from $5 \times 10^9$ cells in 50 ml buffer (300 mM NaCl, 10 mM $Na_2HPO_4$ pH 7.4, 0.2% $NaN_3$w/v 0.5% NP-40 v/v), 0.01% Tween 80 w/v, 0.2 mM phenylmethylsulfonyl fluoride, and 0.1 mM tosyl L-lysine chloromethyl ketone) (0° C.×30 min), centrifuged (4° C. 3000×g×15 min, 23420 ×g×30 min) filtered, precleared×2 over a P3-SEPHAROSE column, and allowed to bind overnight (4° C.) to A3D8-SEPHAROSE. The column was washed with 5 column volumes equilibration buffer, followed by 5 column volumes of 50 mM Tris, pH 7.4, 0.5% NP-40. NP-40 was exchanged for octyl glucoside (OG) (Sigma, St. Louis, Mo.) by washing with 2 column volumes 50 mM Tris pH 7.4, 1.5% OG w/v. CD44 protein was eluted with 2.5 M $MgCl_2$, 50 mM Tris pH 7.4, 1.5% OG and the column regenerated by washing with 0.1 M Tris, 0.5 M NaCl, pH 8.5, then 0.1 M $NaC_2H_3O_2$, 0.5 M NaCl pH 4.5 and finally phosphate buffered saline (PBS). Eluted fractions were dialyzed sequentially against 50 mM Tris pH 7.4+1.5% OG, PBS+1.5% OG, PBS+1.25% OG, and PBS+1% OG using a CENTRIPREP-30 device (Amicon, Danvers, Mass.), and the affinity purification steps repeated until SDS-PAGE silver staining of the resulting CD44 protein preparation revealed only a single band at 80–85 kD that reacted strongly with A3D8 antibody in Western blot analysis.

CD44 Liposomes

Liposomes were prepared by the method of Mimms et al ((1981) Biochemistry 20:833–840), using 1 µM purified CD44 or control glycophorin protein, 1 nM L-α-dioleoyl lecthin (Avanti Polar Lipids, Birmingham, Ala.), and 240 nM OG. Liposomes were analyzed for content of the appropriate protein using a novel labelling technique and flow cytometry. Liposomes were incubated with 5-(N-octadecanoyl) aminofluorescein (Molecular Probes, Eugene, Oreg.) in PBS×10 min at room temperature. Fluoresceinated liposomes were then reacted with 4.5 mm magnetic beads (Dynabeads M-450 Goat anti-Mouse IgG, Dynal Inc., Great Neck, N.Y.) coated with CD44 (A3D8) or anti-glycophorin (E3,E4,E5) mAbs. After 45 minutes (4° C.), with continuous end-over-end rotation, beads were washed ×3 in PBS using a magnet to immobilize the beads during PBS changes. Fluoresceinated liposome-bead conjugates were then analyzed by flow cytometry.

T Cell Activation Assay

PBMC from healthy donors were stimulated with optimal mitogenic concentration of CD2 mabs 35.1 and 9-1 as described (Denning et al). Where indicated, CD44 or control glycophorin liposomes (final protein range used was 28–140 nM) were added to these cultures 20 min prior to addition of CD2 mabs. In some experiments PBMC were pretreated with 0.1% bromelain to remove cell membrane CD44 (Telen et al (1983) J. Clin. Invest. 71:1878–1886, Hale (1989) Immunol. 143:3944–3948).

EXAMPLE 1

Figure 1G:
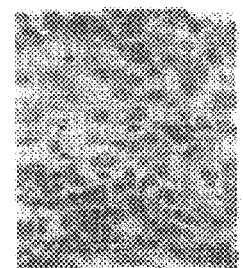
Figure 1H:
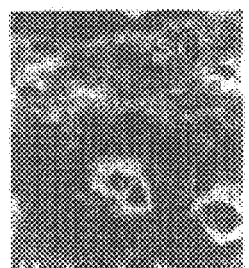
Figure 1I:
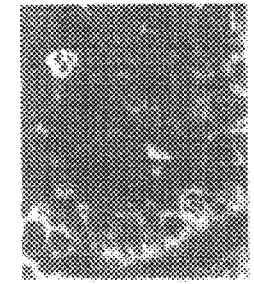
Figure 1J:
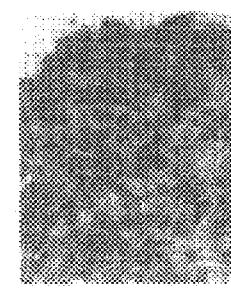
Figure 1K:
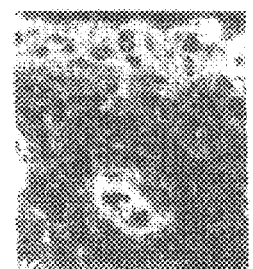
Figure 1L:

Histologic Analysis of Expression of CD44 and Fibronectin in Trauma Synovium, OA and RA CD44 expression was studied in synovial tissues from 7 RA and 8 OA patients who had surgery for joint replacement and 6 patients who had joint surgery due to joint trauma (Table 2). As a control for CD44, synovial tissue expression was also studied of the extracellular matrix protein, fibronectin. Previous studies have shown fibronectin deposition to be increased in synovial tissues in RA (Scott et al. (1991) Brit. J. Exp. Pathol. 62:362–368). Both CD44 and fibronectin expression were found to be dramatically unregulated in RA synovial tissue compared to their expression in OA or non-inflammed trauma synovium (FIG. 1). In trauma and OA synovium, CD44 and anti-fibronectin mabs reacted with synovial lining cells, vessels and fibroblasts (FIGS. 1A–F). In RA, infiltrating lymphocytes and macrophages, as well as synovial lining cells, vessels and fibroblasts were brightly CD44+ (FIGS. 1G,H,I). In RA with pannus formation, both CD44 and fibronectin were widely expressed throughout synovial tissues (FIGS. 1K,J,L). RA tissues studied had a mean inflammation score of 13.1±2.0 versus 6.6±1.3 in OA tissues. The degree of CD44 mAb reactivity in indirect IF assay was graded (CD44 index, see Methods) on a 1–4 scale with 1 the least CD44 present and 4 the most. The mean CD44 index in RA was 3.6±0.2 versus 1.8±0.2 in OA ($p<0.001$) (Table 3). Thus, CD44 upregulation in synovial tissues in RA was due to two separate mechanisms: 1) increase in expression of CD44 on synovial tissue cell types (synovial lining cells, vessels, fibroblasts), and 2) influx of CD44+infiltrating immune cells (CD44+T and B lymphocytes, macrophages).

TABLE 2

Characteristics of Patients From Whom Synovial Tissue Was Obtained For Study

| Patient | Age | Disease | Duration | Medications at Surgery | Tissue Site | Inflam. Score | CD44 Index | Fibro. Index |
|---|---|---|---|---|---|---|---|---|
| RA | | | | | | | | |
| 154 | 68 | RA | 8 yrs | Pred | Knee | 21 | 4+ | 4+ |
| 146 | 60 | RA | >20 yrs | Pred, Mtx | Knee | 13 | 4+ | 4+ |
| 90 | 61 | RA | 5 yrs | NSAID, Mtx | PIP | 14 | 3+ | 3+ |
| 86 | 72 | RA | >10 yrs | NSAID, ASA | Knee | 18 | 3+ | 4+ |
| 38 | 68 | RA | 16 yrs | NSAID, ASA | Knee | 8 | 4+ | 4+ |
| 7 | 62 | RA | 10 yrs | ASA, Pred, NSAID, Au | PIP | 13 | 4+ | 4+ |
| 127 | 59 | RA | 15 yrs | Pred, TLI | Shoulder | 5 | 3+ | 4+ |
| OA | | | | | | | | |
| 20 | 58 | OA | 10 yrs | ASA, IAS | Knee | 8 | 2+ | 4+ |
| 11 | 71 | OA | 10 yrs | ASA | Knee | 8 | 2+ | 3+ |
| 36 | 60 | OA | 5 yrs | None | Hip | 5 | 1+ | 1+ |
| 198 | 60 | OA | 2 yrs | NSAID | Hip | 3 | 2+ | 2+ |
| 242 | 78 | OA | 8 yrs | NSAID | Knee | 14 | 3+ | 4+ |
| 244 | 71 | OA | 13 yrs | NSAID | Knee | 4 | 2+ | 2+ |
| 169 | 81 | OA | 7 mo. | NSAID | Shoulder | 8 | 1+ | 2+ |
| 237 | 74 | OA | 20 yrs | NSAID | Knee | 3 | 1+ | 1+ |
| Trauma | | | | | | | | |
| 148 | 72 | Trauma | 4 mo. | NSAID | Shoulder | 5 | 1+ | 1+ |
| 212 | 42 | Trauma | 1 yr | NSAID | Elbow | 25 | 3+ | 4+ |

TABLE 2-continued

Characteristics of Patients From Whom Synovial Tissue Was Obtained For Study

| Fibro. Patient | Age | Disease | Duration | Medications at Surgery | Tissue Site | Inflam. Score | CD44 Index |
|---|---|---|---|---|---|---|---|
| 211<br>4+ | 22 | Trauma | 6 mo. | None | MTP | 10 | 3+ |
| 229<br>2+ | 35 | Trauma | 1 yr | ASA | Toe | 5 | 1+ |
| 161<br>1+ | 36 | Trauma | 19 yrs | None | PIP | 1 | 1+ |
| 250<br>1+ | 52 | Trauma | 9 mo. | None | MCP | 4 | 1+ |

Pred, prednisone
Mtx, methotrexate
NSAID, non-steroidal anti-inflammatory agent
ASA, aspirin
Au, gold therapy
TLI, total lymphoid irradiation
IAS, intraarticular steroids
The diagnosis of RA was made using ACR criteria.

TABLE 3

Mean Inflammation Score, CD44 Index and Fibronectin Index in RA, OA, and Traumatic Synovium Tissues*

| Disease | Inflammation Score | CD44 Index | Fibronectin Index |
|---|---|---|---|
| Trauma (n = 6) | 9.2 ± 4.2# | 2.0 ± 0.4 | 2.4 ± 0.6 |
| OA (n = 8) | 6.6 ± 1.3 | 1.9 ± 0.2 | 2.3 ± 0.6 |
| RA (n = 7) | 13.1 ± 2.0 | 3.6 ± 0.2** | 3.8 ± 0.1** |

*all values mean ± SEM
**$p < .001$ when compared to trauma or to OA
trauma mean inflammatory index varied from specimen to specimen, range (1–25). No. 229 (inflammation index = 5) was used as a control tissue in biochemical studies.

TABLE 4

Mean Relative CD44 Protein Levels in OA and RA Synovial Tissues Determined by Western Blot Analysis

| Disease | Inflammation Score | CD44 Index* | CD44 Protein Level# |
|---|---|---|---|
| OA (n = 5) | 6.4 ± 2.1 | 2.0 ± 0.3 | 3.5 ± 0.7 |
| RA (n = 3) | 17.3 ± 2.3 | 4.0 ± 0@ | 10.7 ± 1.7** |

*CD44 index determined by histologic IF analysis.
CD44 protein level determined by quantitative Western blot analysis.
Data are arbitrary units relative to CD44 levels found in trauma synovium no. 229 (relative CD44 level = 1, inflammatory index = 5).
@$p < .01$ when compared to OA.
**$p < .005$ when compared to OA.

EXAMPLE 2

Figure 2A:
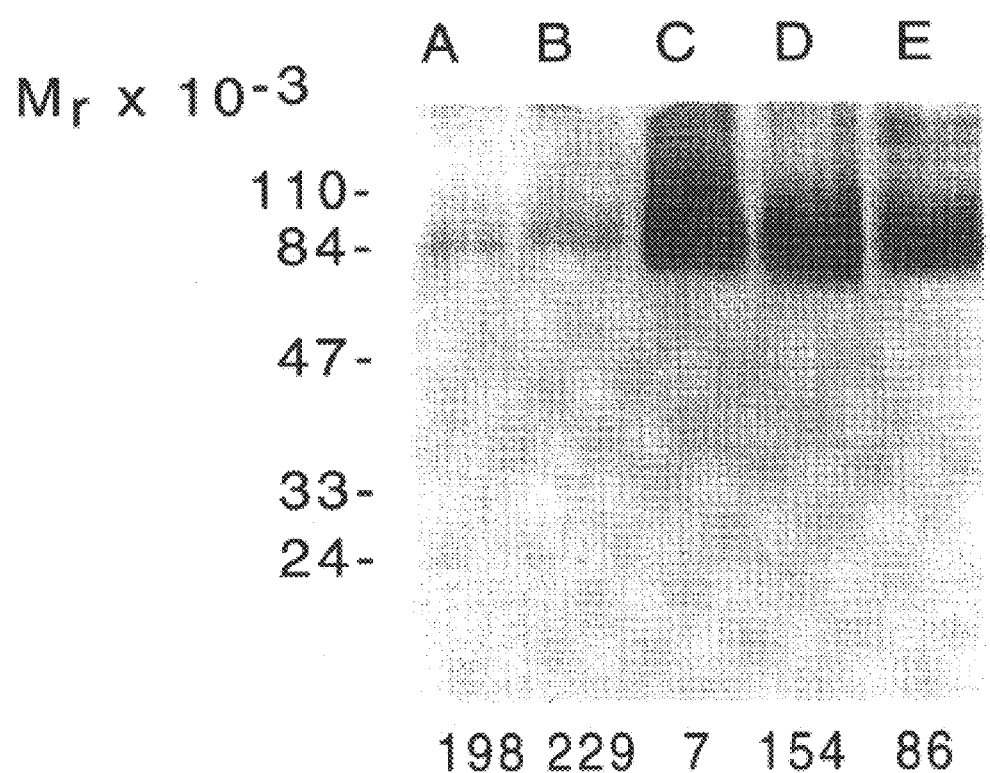
FIGS. 2A–B. Quantitative Western Blot Analysis of CD44 Protein in Synovial Tissue. Equal amounts of tissue were extracted from each synovium and run on SDS-PAGE followed by Western blot analysis with anti-CD44 mab A3D8.
Figure 2B:
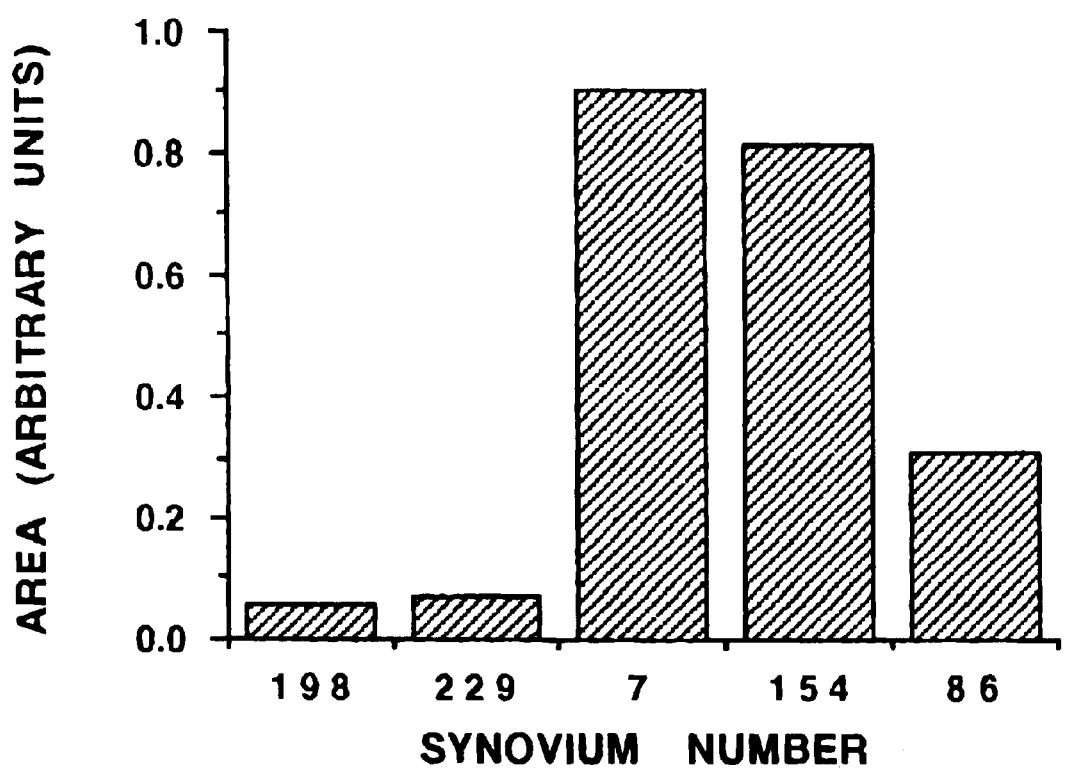

Direct Quantitative Assay of the Relative Amount of CD44 Protein in Synovial Tissue The relative amount of CD44 in synovial tissue was determined in 5 OA (nos. 244,169,237,242, and 148), and in 3 RA (nos. 154,86, and 7) tissues using quantitative Western blot analysis (Table 4). Analysis of the 5 OA synovial tissues demonstrated a mean relative amount of CD44 by Western blot of 3.5±0.7 (ie an average of 3.5×more CD44 than in trauma synovial tissue no. 229). In contrast, RA synovial tissues contained a mean relative amount of CD44 by Western blot of 10.7±1.7 (Table 4). A representative Western blot of CD44 levels in trauma synovium (no. 229), RA synovium (nos. 7,154, and 86) and in a representative OA synovium (no. 198) is shown in FIG. 2A. FIG. 2B shows the relative amounts of CD44 in each synovial tissue as determined by the actual value obtained by laser densitometry of the same Western blot gel. Thus, quantitative Western blot analysis demonstrated RA tissue contained 3 fold more CD44 per gram of wet tissue than did OA tissue, 11 fold more than trauma synovium, and demonstrated that the amount of synovial tissue CD44 correlated with the degree of inflammation present (Table 4).

EXAMPLE 3

Figure 3:
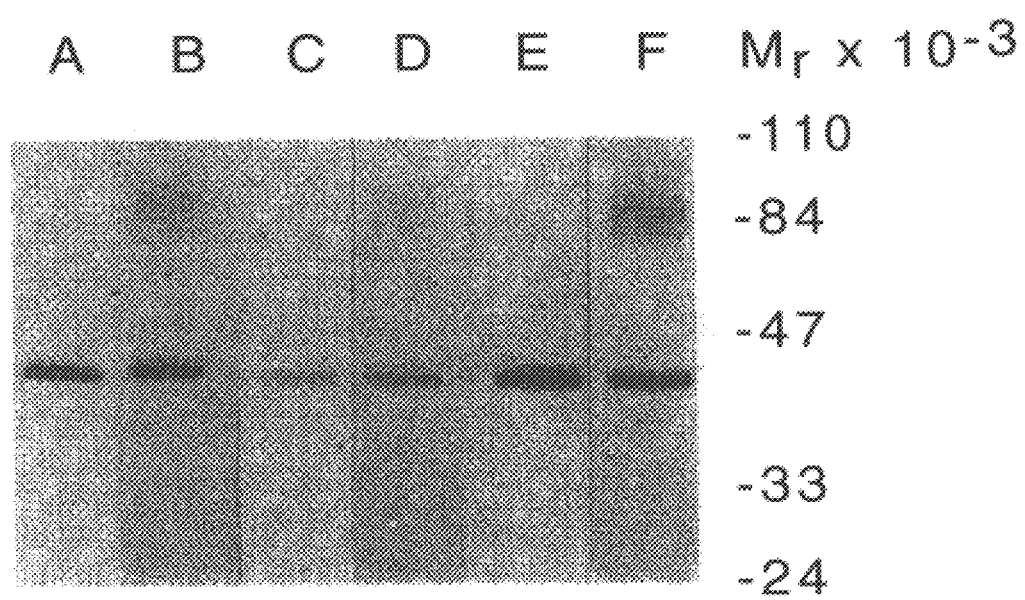
FIG. 3. Western Blot Analysis of CD44 Protein in Trauma, OA and RA Synovial Fluid. Lanes A, C, and E are control lanes in which CD44 protein was immunoprecipitated with CD44 mab and then run in Western blot analysis and blotted with control P3X63/Ag8 IgGl paraprotein. Lanes B, D, and F are CD44 protein immunoprecipitated with CD44 mab and then blotted with CD44 mab. Lanes A and B are from synovial fluid no. 11 (trauma, cell count 450, relative CD44 level=1.0) lanes C and D are from synovial fluid no. 29 (OA, cell count 3,469, CD44 level=0.77) and lanes E and F from RA synovial fluid 13 (cell count 11,061, CD44 level 1.69).
Figure 4:
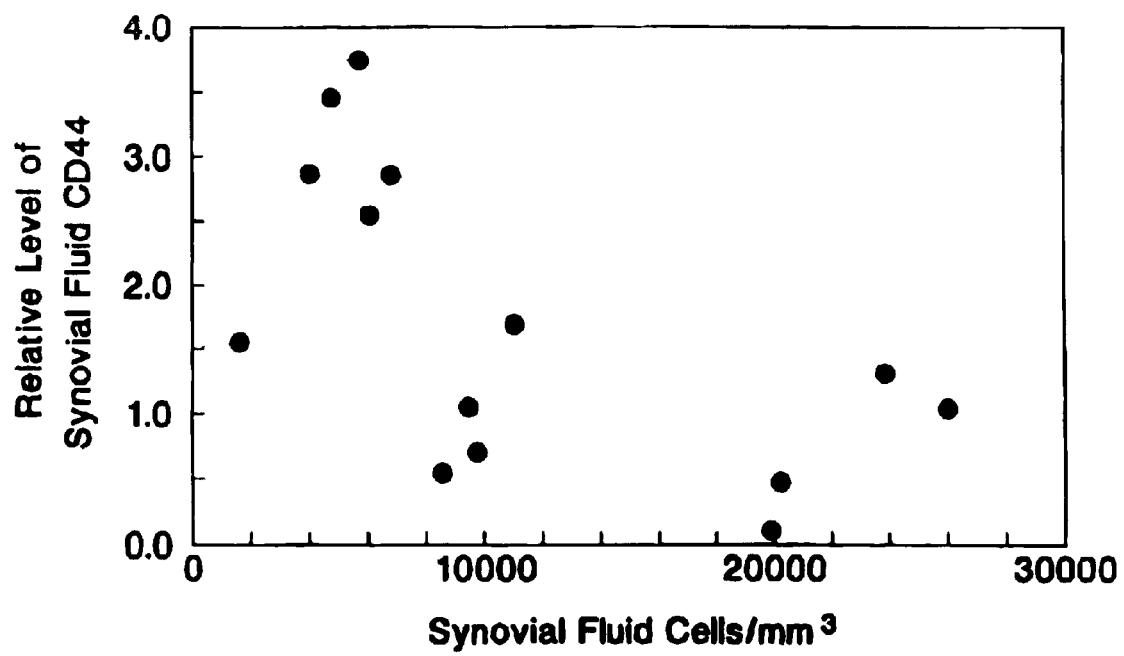
FIG. 4. Comparison of RA Synovial Fluid Cell Counts Versus Relative Levels of Synovial Fluid CD44 Protein.

Comparison of the Relative Levels of Soluble CD44 in RA Versus OA Synovial Fluid Because CD44 protein has been shown to circulate in a soluble form in plasma and serum (Telen et al (1983) J. Clin. Invest. 71:1878–1886), a determination was made whether the soluble CD44 was present in trauma, RA and OA synovial fluid. For this analysis, immunoprecipitation of CD44 antigen from 200 $\mu$l of synovial fluid followed by quantitative Western blot analysis was used. In 5 OA synovial fluids studied, the mean WBC was 1250±577 cells/mm$^3$ and the mean level of CD44 was 0.94±2 [ie, was 0.94× the level of CD44 found in trauma synovial fluid no. 11]. In RA synovial fluid, the mean cell count was elevated (11, 279±2107) ($p<0.025$ compared to OA) and the mean CD44 level was near double that of trauma and OA synovial fluid (1.91±0.4) ($p<0.001$) (Table 5). FIG. 3 shows examples of CD44 in RA versus OA and trauma synovial fluids. Thus, RA synovial fluid contained an average of 2 fold more soluble CD44 than OA or trauma synovial fluid, and the mean RA synovial cell count was higher than for OA (Table 5). However, when individual RA synovial fluid cell counts were plotted versus the relative level of RA synovial fluid CD44, a significant trend was observed to be present such that higher CD44 levels occurred in synovial fluid samples with lower cell counts (Spearman Rank order correlation, $r=-0.68$, $p<0.01$) (FIG. 5). When RA synovial fluids were grouped according to cell count, RA synovial fluids with low cell counts (<7000 cells/mn$^3$) had 3.3× (2.84±0.3 mean±SEM relative CD44 level) more CD44 than did RA synovial fluids with higher cell counts (>8500 cells/mm$^3$) (0.85±0.35 mean±SEM relative CD44 level). Thus, higher levels of soluble CD44 were present in RA synovial fluids with lower cell counts, and synovial fluid CD44 decreased to sub-normal levels in the more inflammatory RA synovial fluids.

TABLE 5

Quantitation of CD44 Levels in OA and RA Synovial Fluid

| Patient | Diagnosis | Cell Count (mm$^3$) | CD44 Protein Level |
|---|---|---|---|
| 18 | RA | 1,634 | 1.55 |
| 31 | RA | 4,047 | 2.87 |
| 25 | RA | 4,776 | 3.45 |
| 6 | RA | NA | 4.81 |
| 26 | RA | 5,737 | 3.74 |
| 22 | RA | 6,080 | 2.55 |
| 30 | RA | 6,820 | 2.87 |
| 15 | RA | 8,565 | 0.54 |
| 23 | RA | 9,472 | 1.05 |
| 33 | RA | 9,772 | 0.70 |
| 13 | RA | 11,061 | 1.69 |
| 17 | RA | 19,840 | 0.00 |
| 12 | RA | 20,214 | 0.47 |
| 35 | RA | 23,867 | 1.31 |
| 34 | RA | 26,024 | 1.04 |
| | mean ± SEM | 11,279 ± ,107 | 1.91 ± 0.36 |
| 5 | OA | 98 | 1.38 |
| 16 | OA | 798 | 1.24 |
| 24 | OA | 831 | 0.57 |
| 10 | OA | 1,072 | 0.73 |
| 29 | OA | 3,469 | 0.77 |
| | mean ± SEM | 1,250 ± 577 | 0.94 ± 0.16 |

*Data are arbitrary units relative to CD44 level found in trauma synovial fluid no. 11 (cell count 450, relative CD44 protein level taken as 1.0). The types of medications taken by RA patients with WBC >8500 did not differ from medications taken by RA patients with WBC <7000. RA Patient 17 also had calcium pyrophosphate crystals present in join fluid.

EXAMPLE 4

Figure 5A:
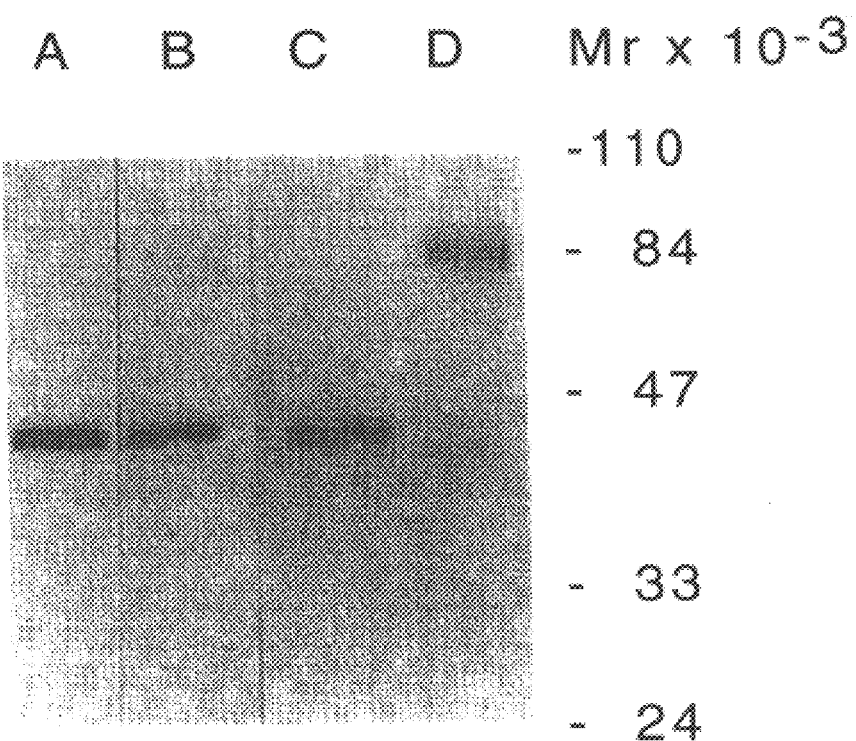
FIGS. 5A–B. Western Blot Analysis of CD44 Protein in Synovial Fluid from non-RA Types of Inflammatory Synovitis.
Figure 5B:
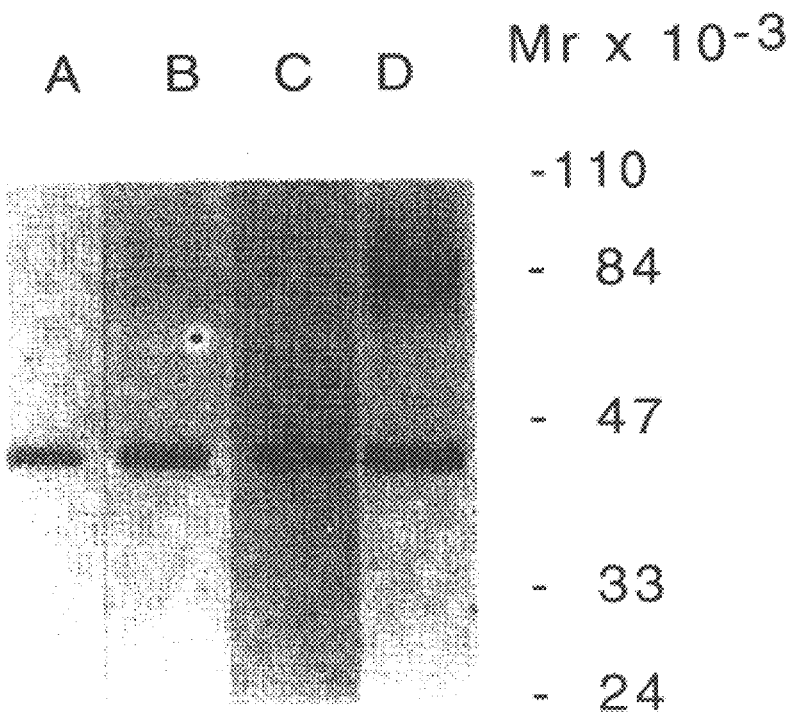
Figure 6:
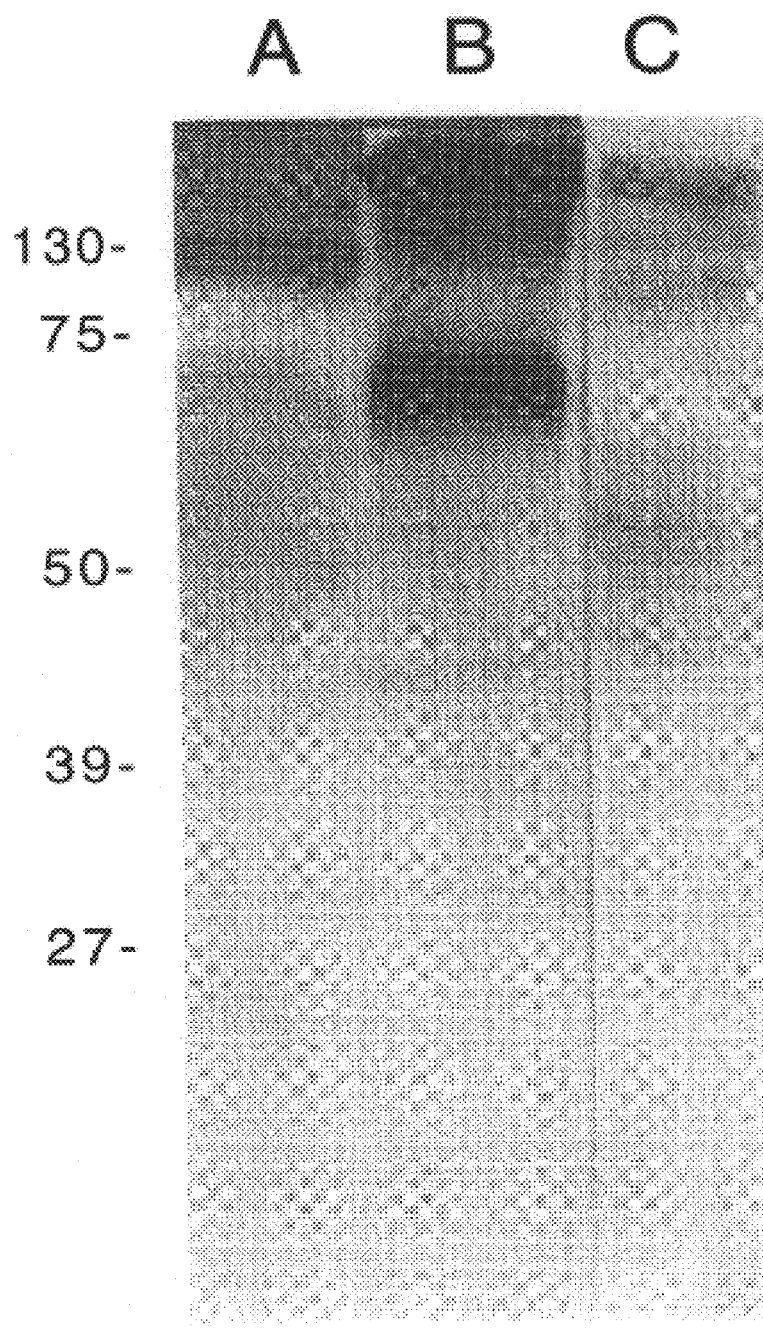
FIG. 6. Shows a western blot analysis of recombinantly produced CD44-Rg-2 protein that could be used as an immunosuppressive agent to inhibit CD44-mediated proinflammatory functions.

Effect of Elevated Synovial Fluid Cell Counts on Soluble CD44 Levels in Non-RA Forms of Inflammatory Synovitis To determine if elevated synovial fluid cell counts of >8500 /mm$_3$ were associated with normal or depressed synovial fluid CD44 levels in diseases other than RA, 3 non-RA inflammatory synovial fluids were studied, no.14 (*Staphylococus aureus* septic arthritis, cell count, 371,915/ mm$^3$), no. 32 (gout, cell count, 35,400 /mm$^3$) , and no.100 (psoriatic arthritis, cell count, 9294/mm$^3$). CD44 levels were elevated in all three cases above the mean CD44 found level in high-cell-count RA fluid (no. 14, CD44 level=2.45; no.32, CD44 level=3.79; no. 100, CD44 level=7.00) (FIGS. 5A, 5B). Thus, decrease of RA synovial fluid CD44 levels in the presence of higher (>8500/mm$^3$) cell count was not a general phenomenon related solely to the number of synovial inflammatory cells present.

EXAMPLE 5

Effect of Soluble CD44 Protein on T Cell Activation

Because soluble CD44 antigen levels decreased in RA synovial fluids with high cell counts but not in gout or in other non-RA inflammatory synovial fluids, and because cell-associated CD44 is involved in T cell activation (Denning et al. (1989) J. Immunol. 142:2988–97, Huet et al (1989) Immunol. 143:798–801, Shimuzu et al (1989) J. Immunol. 143:2457–2463), potential immunologic sequelae of decreased levels of soluble CD44 in inflammatory RA synovial fluids on T cell function were determined. To directly assess the effect of soluble CD44 protein on T cell activation, CD44 was affinity-purified from T cell membranes, incorporated into liposomes, and incubated with peripheral blood mononuclear cells (PBMC) prior to stimulation with CD2 antibodies (a potent stimulus of T cell activation) (Denning et al. (1989) J. Immunol. 142:2988–97, Stamenkovic et al. (1989) Cell 56:1057–1062). Initial experiments showed that CD44 protein-containing liposomes alone had no effect on the proliferation of T cells (data not shown). However, when CD44 protein-containing liposomes (CD44 concentration 140 nM) were added to PBMC prior to addition of CD2 antibodies, T cell proliferation was significantly decreased by 35±4% (n=4, p<0.02) (Table 6) as compared to addition of control (glycophorin-containing) liposomes. The cysteine protease, bromelain, was previously shown to remove surface CD44 from T cells (Telen et al., Hale et al (1989) Immunol. 143:3944–3948). As a control, no suppression of T cell activation was observed when CD44 protein-containing liposomes were added to bromelain-treated PBMC (average suppression 0.5±7%, n=3, p=NS) (Table 6).

TABLE 6

Effect of Soluble CD44 Protein on CD2-Mediated T Cell Activation

| Treatment | Additions to Culture | cpm/10$^6$ Cells |
|---|---|---|
| Sham treated PBMC | Media | 460 |
| | CD2 mAb | 308,230 |
| | CD2 mAb + CD44 liposomes | 172,960 |
| | CD2 mAb + control liposomes | 255,090 |
| Bromelain-treated PBMC | Media | 5,380 |
| | CD2 mAb | 552,440 |
| | CD2 mAb + CD44 liposomes | 646,830 |
| | CD2 mAb + control liposomes | 550,000 |

*Data shown is from a single experiment representative of 4 experiments with sham-treated cells and 3 matched experiments with bromelain-treated cells. Protein concentration for both CD44 and glycophorin liposomes added in this experiment was 140 nM. The mean suppression of CD2 proliferation by sham-treated PBMC in the presence of CD44 liposomes in 4 separate experiments was 35 ± 4% (mean ± SEM) as compared to control liposomes (p < 0.02, paired t-test). Addition of CD44 liposomes to bromelain treated PBMC had no significant effect on CD2-mediated proliferation (mean increase 5 ± 7% (p = NS) as compared with control liposomes. Identical results were obtained when soluble, free CD44 protein was added to CD2 stimulated PBMC cultures (Data not shown).

* * * *

In a further embodiment, the present invention relates to a method of preventing or treating HIV infections.

HIV causes the acquired immunodeficiency syndrome (AIDS) and death in humans. Treatments to prevent and/or eliminate infection in humans are quite limited, with the only proven beneficial treatment being zidovudine. In vitro studies have documented that HIV infects human lymphocytes and mononuclear phagocytes by way of adherence of virus gp 120 to cellular membrane CD4. CD4 or anti-CD4 antibodies block HIV infection, but this is usually not complete. Auxiliary cellular receptors for HIV (other than CD4) have been postulated, but these have not been demonstrated. Clinical studies with soluble CD4 given to humans are being done now; preliminary results are apparently demonstrating no significant benefit.

This aspect of the present invention provides a new method, based on a separate molecular pathway, of blocking HIV infection. The invention is based, at least in part, on Applicants' observation that CD44 (the hyaluronate receptor) facilitates HIV infection/expression in human cells. When this molecule is "blocked"by binding to the anti-CD44 antibody A3D8 or AlG3, there is a 40–80% reduction of HIV infection/expression in normal human monocytes in vitro, as determined by inhibition of monocyte polykaryon formation and expression of viral reverse transcriptase in supernatant medium. Likewise, hyaluronate (or hyaluronic acid), the natural ligand of CD44, inhibits infection/expression up to 85% (ID50=5 µg/ml). Chondroitin sulfate, a polyanion which does not bind to CD44, has no or minimal inhibitory activity.

Accordingly, this aspect of the present invention broadly relates to a method of preventing/treating HIV infection comprising contacting cells susceptible to HIV infection with an agent that inhibits HIV entry into such cells. Agents suitable for use in the above-described method include anti-CD44 antibodies (e.g., A3D8 or AlG3); soluble CD44, including recombinantly produced CD44; CD44 oligopeptides (e.g., CD44 peptides 1–10 set forth in Table 1); and hyaluronate. Chimeric molecules of CD44 with immunoglobulin can also be used, such molecules producing a lengthened circulation of CD44. These agents can be used alone or in combination with, for example, other compounds that block cellular receptors for HIV infection (e.g. soluble CD4) as well as reverse transcriptase inhibitors, such as zidovudine.

The agents suitable for use in the present method can be used alone or in combination, for example, for post-exposure prophylaxis therapy. Administration can be parenteral or loco-regional (for example, intravaginally).

One skilled in the art will appreciate that the above-referenced agents can be used in combination with alternative forms of HIV therapy to, for example, decrease the number of HIV-infected cells or to decrease the spread of virus from cell to cell. These agents can also be used to lessen the infectability of HIV in products designed for infusion into humans (e.g., blood derived transfusion products). Further, these agents can be used to prevent HIV infection or spread of HIV infection in cells, including human cells in vitro (e.g., blood cells). In addition, these agents can be used as reagents for the experimental analysis of HIV infection of cells in vitro.

This aspect of the invention is described in further detail in the following non-limiting Example.

EXAMPLE

To determine the importance of other monocyte cellular surface molecules in in vitro infection with HIV-1, the abilities of various murine monoclonal antibodies directed toward different monocyte membrane antigens to influence HIV-1 infection of human monocytes in vitro were determined. Monocytes from normal people were isolated by density gradients, adherence, and washing. Cells were inoculated with HIV-1$_{Ba.L.}$ with or without three weeks of culture for reverse transcriptase (RT) activity, and the plates were examined morphologically. Antibodies AlG3 and A3D8 (anti-CD44 antibodies) reduced HIV-1-induced cytopathology and decreased supernatant RT, whereas an anti-Class I MHC antibody (3F10) had no effect. With A3D8, this effect appeared to be dose-related and disappeared gradually with increasing dilutions of the antibody (1:100 to 1:400). Monocytes treated with the CD44 ligand, hyaluronic acid (1–125 µg/ml), had diminished morphological changes and RT expression (ID50≈5 µg/ml). Chondroitin sulfate, a polyanion which does not bind to CD44, had no effect.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 22 amino acids
      (B) TYPE: amino acid
      (D) TOPOLOGY: linear (ii) MOLECULE TYPE: peptide (xi) SEQUENCE DESCRIPTION: SEQ ID NO:1:

Cys Glu Lys Asn Gly Arg Tyr Ser Ile Ser A rg Thr Glu Ala Ala Asp
1            5                  10                 15

Cys Cys Lys Ala Phe Asn
          20

(2) INFORMATION FOR SEQ ID NO:2:

```
          (i) SEQUENCE CHARACTERISTICS:
              (A) LENGTH: 23 amino acids
              (B) TYPE: amino acid
              (D) TOPOLOGY: linear (ii) MOLECULE TYPE: peptide (xi) SEQUENCE DESCRIPTION: SEQ ID NO:2:

Cys Asn Thr Ser Gln Tyr Asp Thr Tyr Cys P he Asn Ala Ser Ala Pro
1               5                  10                  15

Pro Glu Glu Asp Cys Thr Ser
                20

(2) INFORMATION FOR SEQ ID NO:3:

(i) SEQUENCE CHARACTERISTICS:
              (A) LENGTH: 32 amino acids
              (B) TYPE: amino acid
              (D) TOPOLOGY: linear (ii) MOLECULE TYPE: peptide (xi) SEQUENCE DESCRIPTION: SEQ ID NO:3:

Cys Arg Asp Gly Thr Arg Tyr Val Gln Lys G ly Glu Tyr Arg Thr Asn
1               5                  10                  15

Pro Glu Asp Ile Tyr Pro Ser Asn Pro Thr A sp Asp Asp Val Ser Ser
                20                  25                  30

(2) INFORMATION FOR SEQ ID NO:4:

(i) SEQUENCE CHARACTERISTICS:
              (A) LENGTH: 42 amino acids
              (B) TYPE: amino acid
              (D) TOPOLOGY: linear (ii) MOLECULE TYPE: peptide (xi) SEQUENCE DESCRIPTION: SEQ ID NO:4:

Cys Arg Asp Gly Thr Arg Tyr Val Gln Lys G ly Glu Tyr Arg Ile Asn
1               5                  10                  15

Pro Glu Asp Ile Tyr Pro Ser Asn Pro Thr A sp Asp Asp Val Ser Ser
                20                  25                  30

Gly Ser Ser Ser Glu Arg Ser Ser Thr Ser
                35                  40

(2) INFORMATION FOR SEQ ID NO:5:

(i) SEQUENCE CHARACTERISTICS:
              (A) LENGTH: 21 amino acids
              (B) TYPE: amino acid
              (D) TOPOLOGY: linear (ii) MOLECULE TYPE: peptide (xi) SEQUENCE DESCRIPTION: SEQ ID NO:5:

Cys Tyr Arg Thr Asn Pro Glu Asp Ile Tyr P ro Ser Asn Pro Thr Asp
1               5                  10                  15

Asp Asp Val Ser Ser
                20

(2) INFORMATION FOR SEQ ID NO:6:

(i) SEQUENCE CHARACTERISTICS:
              (A) LENGTH: 21 amino acids
              (B) TYPE: amino acid
```

(D) TOPOLOGY: linear (ii) MOLECULE TYPE: peptide (xi) SEQUENCE DESCRIPTION: SEQ ID NO:6:

Cys Thr Val His Pro Ile Pro Asp Glu Asp S er Pro Trp Ile Thr Asp
1               5                   10                  15

Ser Thr Pro Arg Ile
            20

(2) INFORMATION FOR SEQ ID NO:7:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (xi) SEQUENCE DESCRIPTION: SEQ ID NO:7:

Asp Ser Pro Trp Ile Thr Asp Ser Thr Asp A rg Ile Phe Ala Thr Arg
1               5                   10                  15

Asp Gln Asp Thr Ile
            20

(2) INFORMATION FOR SEQ ID NO:8:

(i) SEQUENCE CHARACTERISTICS:
            (A) LENGTH: 35 amino acids
            (B) TYPE: amino acid
            (D) TOPOLOGY: linear (ii) MOLECULE TYPE: peptide (xi) SEQUENCE DESCRIPTION: SEQ ID NO:8:

Cys Ala Thr Arg Asp Gln Asp Thr Phe His P ro Ser Gly Gly Ser His
1               5                   10                  15

Thr Thr His Glu Ser Glu Asp Gly His Ser H is Gly Ser Gln Glu Gly
                20                  25                  30

Gly Ala Asn
        35

(2) INFORMATION FOR SEQ ID NO:9:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:9:

Cys Arg Asp Gly Ile Arg Tyr Val Gln Lys G ly Glu Tyr
1               5                   10

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:10:

Pro Ser Asn Pro Thr Asp Asp (2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

```
Thr Ser Gly Gly Tyr Ile Phe Tyr Thr Phe
1               5                   10
```

(2) INFORMATION FOR SEQ ID NO:12:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:12:

```
Leu Cys Leu Val Pro Leu Ser Leu Ala Gln Ile Asp Leu Asn Ile Thr
1               5                   10                  15
Cys Arg Phe Ala Gly Val Phe His Val Glu Lys Asn Gly Arg Tyr
                20                  25                  30
```

(2) INFORMATION FOR SEQ ID NO:13:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:13:

```
Leu Cys Lys Ala Phe Asn Ser Thr Leu Pro Thr Met Ala Gln Met Glu
1               5                   10                  15
Lys Ala Leu Ser Ile Gly Phe Glu Thr Cys Arg Tyr
                20                  25
```

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:14:

```
Cys Arg Tyr Gly Phe Ile Glu Gly His Val Val Ile Pro Arg Ile His
1               5                   10                  15
Pro Asn Ser Ile Cys
                20
```

(2) INFORMATION FOR SEQ ID NO:15:

(i) SEQUENCE CHARACTERISTICS:
        (A) LENGTH: 19 amino acids
        (B) TYPE: amino acid
        (D) TOPOLOGY: linear

```
    (ii) MOLECULE TYPE: peptide (xi) SEQUENCE DESCRIPTION: SEQ ID NO:15:

Arg Tyr Gly Phe Ile Glu Gly His Val Val I le Pro Arg Ile His Pro
1               5                   10                  15

Asn Ser Ile (2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

Leu Thr Tyr Asn Thr Ser Gln Ty r Asp Thr Tyr
    1               5                   10
```

What is claimed is:

1. A method of inhibiting CD44-facilitated HIV infection of a mononuclear phagocyte susceptible to infection with a strain of HIV comprising contacting said mononuclear phagocyte with an anti-CD44 antibody in an amount such that said antibody binds to CD44 molecules present on the surface of said mononuclear phagocyte and thereby inhibits said CD44-facilitated infection of said mononuclear phagocyte by said strain of a HIV.

2. The method according to claim 1 wherein said anti-CD44 antibody is A3D8.

3. The method according to claim 1 wherein said mononuclear phagocytes are in vitro mononuclear phagocytes.

4. A method of inhibiting, in a patient, CD44-facilitated HIV infection of mononuclear phagocytes susceptible to infection with a strain of HIV comprising administering to said patient an amount of soluble CD44 sufficient to inhibit said CD44-facilitated infection of said mononuclear phagocytes by said strain of a HIV.

5. A method of inhibiting, in a patient, CD44-facilitated HIV infection of mononuclear phagocytes susceptible to infection with a strain of HIV comprising administering to said patient an amount of CD44 oligopeptides sufficient to inhibit said CD44-facilitated infection of said mononuclear phagocytes by said strain of a HIV.

6. The method according to claim 5 wherein said CD44 oligopeptide selected from the group consisting of CD44-1 (SEQ ID NO:1), CD44-2 (SEQ ID NO:2), CD44-3 (SEQ ID NO:3), CD44-4 (SEQ ID NO:4), CD44-5 (SEQ ID NO:5), CD 44-6 (SEQ ID NO:6), CD44-6a (SEQ ID NO:7), CD44-7 (SEQ ID NO:8), CD44-8 (SEQ ID NOS: 9, 10 AND 11), CD44-9 (SEQ ID NO:12), CD44-10 (SEQ ID NO:13), CD44-11 (SEQ ID NO:14), CD44-12 (SEQ ID NO:15), and CD44-13 (SEQ ID NO:16).

7. The method according to claim 1, 4 or 5 wherein said phagocyte is a human monocyte.

8. The method according to claim 1, 4 or 5 wherein said infection is HIV-1 infection.

9. The method according to claim 1, 4 or 5 wherein said mononuclear phagocytes are vaginal cells.

10. The method according to claim 1 wherein said contacting is effected by topical administration.

11. The method according to claim 4 or 5 wherein said administration is topical administration.

12. The method according to claim 1, 4 or 5 wherein said strain of HIV is a monocytotropic strain.

* * * * *